(12) United States Patent
Nakatate et al.

(10) Patent No.: US 10,058,231 B2
(45) Date of Patent: Aug. 28, 2018

(54) LIGHTING STRUCTURE AND ENDOSCOPE (71) Applicant: FUJIKURA LTD., Koto-ku, Tokyo (JP)

(72) Inventors: Kenichi Nakatate, Sakura (JP); Hitoe Iikura, Sakura (JP)

(73) Assignee: FUJIKURA LTD., Tokyo (JP)

( * ) Notice: Subject to any disclaimer, the term of this patent is extended or adjusted under 35 U.S.C. 154(b) by 0 days.

(21) Appl. No.: 14/134,973

(22) Filed: Dec. 19, 2013

(65) Prior Publication Data

US 2014/0107421 A1    Apr. 17, 2014

Related U.S. Application Data

(63) Continuation of application No. PCT/JP2013/062604, filed on Apr. 30, 2013.

(30) Foreign Application Priority Data

Jun. 8, 2012 (JP) ................................. 2012-130858

(51) Int. Cl.
*A61B 1/06* (2006.01)
*A61B 1/00* (2006.01)
(Continued)

(52) U.S. Cl.
CPC ...... *A61B 1/00096* (2013.01); *A61B 1/00165* (2013.01); *A61B 1/00177* (2013.01);
(Continued)

(58) Field of Classification Search
CPC ............ A61B 1/00167; A61B 1/00177; A61B 1/0623
(Continued)

(56) References Cited

U.S. PATENT DOCUMENTS 3,417,745 A * 12/1968 Sheldon ..................... 600/167
4,523,806 A *  6/1985 Kojima .............. A61B 1/00165
                                                              250/492.1
(Continued)

FOREIGN PATENT DOCUMENTS

| CN | 101375786 A | 3/2009 |
| CN | 101449961 A | 6/2009 |

(Continued)

OTHER PUBLICATIONS

Machine Translation of CN 101375786 of record.
(Continued)

*Primary Examiner* — Timothy J Neal
*Assistant Examiner* — Jae Woo
(74) *Attorney, Agent, or Firm* — Sughrue Mion, PLLC (57) ABSTRACT

A lighting structure includes: an optical transmission medium that transmits pumping light and image light; an objective optical system that is disposed at a distal-end portion of the optical transmission medium; a wavelength conversion unit comprising a fluorescent body that receives the pumping light transmitted through the optical transmission medium and irradiates an object with illuminating light; and a wavelength-selective reflective unit that selectively reflects one of a wavelength of the pumping light and a wavelength of the image light, thereby emits pumping light that is incident thereto through the optical transmission medium into the fluorescent body and emits image light that is incident from the object into the optical transmission medium through the objective optical system.

14 Claims, 7 Drawing Sheets

(51) Int. Cl.
| | |
|---|---|
| *G02B 23/26* | (2006.01) |
| *G02B 23/24* | (2006.01) |
| *A61B 1/07* | (2006.01) |
| *A61B 1/313* | (2006.01) |

(52) U.S. Cl.
CPC ........ *A61B 1/00186* (2013.01); *A61B 1/0646* (2013.01); *A61B 1/0653* (2013.01); *A61B 1/0661* (2013.01); *A61B 1/07* (2013.01); *A61B 1/3137* (2013.01); *G02B 23/2461* (2013.01); *G02B 23/2469* (2013.01); *G02B 23/26* (2013.01)

(58) Field of Classification Search
USPC .......................................... 600/129, 170, 178
See application file for complete search history.

(56) References Cited

U.S. PATENT DOCUMENTS

| | | | | |
|---|---|---|---|---|
| 4,604,992 | A | * | 8/1986 | Sato .................. A61B 1/05 348/67 |
| 4,807,597 | A | * | 2/1989 | Tsuno et al. ................ 600/177 |
| 5,624,380 | A | * | 4/1997 | Takayama ........... A61B 1/0058 600/141 |
| 2001/0055462 | A1 | * | 12/2001 | Seibel ........................ 385/147 |
| 2002/0013531 | A1 | * | 1/2002 | Hayashi ........... A61K 49/0034 600/476 |
| 2005/0192480 | A1 | * | 9/2005 | Toriya et al. ................ 600/182 |
| 2005/0211874 | A1 | * | 9/2005 | Takeyama et al. ........ 250/208.1 |
| 2005/0276553 | A1 | | 12/2005 | Kazakevich |
| 2005/0277810 | A1 | * | 12/2005 | Irion ............................. 600/178 |
| 2006/0190006 | A1 | * | 8/2006 | Oka et al. .................... 606/108 |
| 2007/0149858 | A1 | | 6/2007 | Ogawa et al. |
| 2007/0238955 | A1 | * | 10/2007 | Tearney et al. ............. 600/407 |
| 2008/0051632 | A1 | * | 2/2008 | Ito et al. ..................... 600/114 |
| 2008/0062429 | A1 | * | 3/2008 | Liang et al. ................ 356/497 |
| 2008/0221388 | A1 | * | 9/2008 | Seibel et al. ............... 600/109 |
| 2008/0269563 | A1 | * | 10/2008 | Takahashi ................... 600/178 |
| 2009/0097806 | A1 | | 4/2009 | Viellerobe et al. |
| 2009/0306478 | A1 | | 12/2009 | Mizuyoshi |
| 2010/0010314 | A1 | * | 1/2010 | Krattiger et al. ............ 600/182 |
| 2010/0046897 | A1 | | 2/2010 | Toriya et al. |
| 2010/0091385 | A1 | * | 4/2010 | Togino ........................ 359/736 |
| 2010/0134607 | A1 | * | 6/2010 | Ishihara ......................... 348/68 |
| 2010/0172148 | A1 | | 7/2010 | Komazaki et al. |
| 2010/0280322 | A1 | | 11/2010 | Mizuyoshi |
| 2011/0268141 | A1 | * | 11/2011 | Nakatate ......................... 372/6 |
| 2012/0283516 | A1 | * | 11/2012 | Kang et al. .................. 600/182 |

FOREIGN PATENT DOCUMENTS

| | | | |
|---|---|---|---|
| CN | 101568296 | A | 10/2009 |
| CN | 101609207 | A | 12/2009 |
| DE | 102008039666 | * | 1/2010 |
| DE | 102008039666 | B3 | 1/2010 |
| EP | 2123213 | A2 | 11/2009 |
| JP | 2005-091134 | A | 4/2005 |
| JP | 2005-284194 | A | 10/2005 |
| JP | 2009-510539 | A | 3/2009 |
| JP | 2009-297141 | A | 12/2009 |
| JP | 2010-035922 | A | 2/2010 |
| JP | 2010-069291 | A | 4/2010 |
| JP | 2010-512912 | A | 4/2010 |
| JP | 2010-160948 | A | 7/2010 |
| JP | 4504438 | B2 | 7/2010 |
| JP | 2011-182871 | A | 9/2011 |
| WO | 2007/040390 | A1 | 4/2007 |
| WO | 2008/078254 | A1 | 7/2008 |

OTHER PUBLICATIONS

Machine Translation of JP 2005-091134 of record.
Machine Translation of JP 2010-035922 of record.
Machine Translation of CN 101449961 of record.
Machine Translation of CN 101609207 of record.
Machine Translation of JP 2005-284194 of record.
Machine Translation of JP 2009-297141 of record.
Communication dated Mar. 16, 2015 from the State Intellectual Property Office of the People's Republic of China in counterpart application No. 201380001742.X.
International Search Report for PCT/JP2013/062604 dated Aug. 6, 2013.
Notice of Allowance for JP 2012-130858 dated Sep. 3, 2013.
Office Action issued by Chinese Patent Office Action in Chinese Patent Application 201380001742.X dated Jul. 25, 2014.
Communication dated Jan. 27, 2015 from the European Patent Office in counterpart application No. 13800338.9.

* cited by examiner

LIGHTING STRUCTURE AND ENDOSCOPE

CROSS REFERENCE TO RELATED APPLICATIONS

This application is a continuation application based on a PCT Patent Application No. PCT/JP2013/062604, filed Apr. 30, 2013, whose priority is claimed on Japanese Patent Application No. 2012-130858 filed on Jun. 8, 2012, the content of which is hereby incorporated by reference.

BACKGROUND OF THE INVENTION

The present invention relates to a lighting structure used for an optical observation device such as an endoscope, and an endoscope using the same.

DESCRIPTION OF THE RELATED ART

Conventionally, a side-viewing endoscope transmits illuminating light to a distal end of the endoscope through a bundle (fiber bundle) of an optical fiber that transmits the illuminating light (a multi-component glass fiber having approximately 30 to 50 µm is commonly used), changes the illumination direction of the illuminating light emitted from the end of the optical fiber into a viewing field direction, performs light guiding, and emits the light.

At this time, as a method of changing the illumination direction, a method of directly bending the distal-end portion of the optical fiber, a bending method using a prism, and a method of changing an emitting direction thereof by causing light to be incident to be a curved conduit rod or the like, are used.

Additionally, it is also proposed that transmission of illuminating light and transmission of an image are carried out by use of an image fiber or the like on the same axis (refer to Japanese Unexamined Patent Application, First Publication No. 2010-69291) and fluorescence from a fluorescent body is used as illumination by causing pumping light to be incident to the fluorescent body provided at the distal end of an endoscope (refer to Japanese Patent No. 4504438, Japanese Unexamined Patent Application, First Publication No. 2010-160948, and Japanese Unexamined Patent Application, First Publication No. 2011-182871).

In the transmission of illuminating light using a fiber bundle and in view of a space in which the distal-end portion of the fiber bundle used for changing the illumination direction is bent or an optical component such as a prism or a conduit rod is provided, it is difficult to manufacture a small-diameter endoscope (particularly, used for observing an inner blood vessel or the like, the outer diameter thereof is 1 mm or less).

An increase in loss or wire breakage which is due to flexion of the fiber, or degradation in mechanical reliability may occur.

Furthermore, since the object distance is made short in the side-viewing endoscope, an illumination method or an illumination area is not sufficiently obtained or the range of vision cannot be sufficiently-illuminated; and since uniform illumination is difficult, halation or the like occurs, resulting in degradation in image quality.

In proposals that transmission of illuminating light and transmission of image are carried out on the same axis as described in Japanese Unexamined Patent Application, First Publication No. 2010-69291 or transmission of pumping light and transmission of image are carried out on the same axis as described in Japanese Patent No. 4504438, for example, the illuminating light is reflected by the fiber incident end face, scatter reflections occur at the object side, and degradation in contrast thereby occurs.

In proposals that transmission of illuminating light and transmission of image are separately carried out as described in Japanese Unexamined Patent Application, First Publication No. 2010-160948 and Japanese Unexamined Patent Application, First Publication No. 2011-182871, the outer diameter increases, and it is difficult to manufacture a small-diameter endoscope.

SUMMARY OF THE INVENTION

The invention was conceived in view of the above-described circumstances and has an object thereof to provide a lighting structure and an endoscope using this, in which a diameter of an optical observation device such as an endoscope is easily reduced, halation is less easily generated, and it is possible to realize uniform illumination.

In order to solve the above-described problem, a lighting structure related to a first aspect of the invention includes: an optical transmission medium that transmits pumping light and image light therethrough; an objective optical system that is disposed at a distal-end portion of the optical transmission medium; a wavelength conversion unit including a fluorescent body that receives the pumping light transmitted through the optical transmission medium and irradiates an object with illuminating light; and a wavelength-selective reflective unit that selectively reflects one of a wavelength of the pumping light and a wavelength of the image light, thereby emits pumping light that is incident thereto through the optical transmission medium into the fluorescent body and emits image light that is incident from the object into the optical transmission medium through the objective optical system.

In the lighting structure of the aforementioned first aspect of the invention, it is preferable that the pumping light be ultraviolet light, and the wavelength-selective reflective unit include a wavelength filter that allows the ultraviolet light to transmit therethrough and allows visible light to reflect.

In the lighting structure of the aforementioned first aspect of the invention, it is preferable that the pumping light be blue or purple visible light, and the wavelength-selective reflective unit include a band-pass filter that allows a wavelength of the pumping light to transmit therethrough.

In the lighting structure of the aforementioned first aspect of the invention, it is preferable that the objective optical system be formed in a cylindrical shape that is on the same axis as that of the optical transmission medium and has the same diameter as that of the optical transmission medium.

It is preferable that the lighting structure of the aforementioned first aspect of the invention further include a noise removal filter at an eyepiece system.

In the lighting structure of the aforementioned first aspect of the invention, it is preferable that the fluorescent body be dispersed in glass or resin.

In the lighting structure of the aforementioned first aspect of the invention, it is preferable that the wavelength conversion unit include a mirror or a filter which adjusts a direction, an intensity, or a transparency range of the pumping light or the illuminating light.

In the lighting structure of the aforementioned first aspect of the invention, it is preferable that an aperture, an iris, or a filter be provided which prevents returned light from being incident to the optical transmission medium, serves as a means of reducing an amount of the returned light, and is provided between the wavelength-selective reflective unit and the wavelength conversion unit; and that an aperture, an iris, or a filter be provided which prevents returned light from being incident to a front end of the optical transmission medium, serves as a means of reducing an amount of the returned light, and is provided between the wavelength-selective reflective unit and the wavelength conversion unit.

In the lighting structure of the aforementioned first aspect of the invention, it is preferable that the pumping light be incident to a part of a cross-sectional area of the optical transmission medium and light guiding be thereby carried out.

It is preferable that the lighting structure of the aforementioned first aspect of the invention further include a mask or a filter which prevents noise light, that is from the optical transmission medium, from being incident to an image-sensing device such as a camera that converts the image light into an electrical signal.

Furthermore, an endoscope related to a second aspect of the invention includes the lighting structure of the aforementioned first aspect of the invention.

The endoscope of the aforementioned second aspect of the invention may be a side-viewing endoscope.

In the aforementioned second aspect of the invention, the outer diameter of the distal-end portion thereof is a small diameter of 1 mm or less.

The endoscope of the aforementioned second aspect of the invention may be used for observing an inner blood vessel.

EFFECTS OF THE INVENTION

According to the lighting structure related to the aspect of the invention, since the pumping light and the image light are transmitted through the same optical transmission medium, reduction in a diameter of an optical observation device such as endoscope is easy.

Furthermore, since the illuminating light emitted from the fluorescent body scatters therein, halation is difficult to occur, uniform illumination can be realized, and it is possible to make the illumination area large.

Additionally, as a result of disposing the wavelength-selective reflective unit between the optical transmission medium and the fluorescent body, the fluorescent body can be arranged in a direction that is different from that of an object as seen from the wavelength-selective reflective unit; therefore, even where the illuminating light emitted from the fluorescent body is incident to the wavelength-selective reflective unit, since it is possible to emit in the direction that is different from the optical transmission medium, it is possible to prevent contrast from being degraded.

DETAILED DESCRIPTION OF THE INVENTION

Hereinafter, the invention will be described based on preferred embodiments of the invention with reference to drawings.

Figure 1:
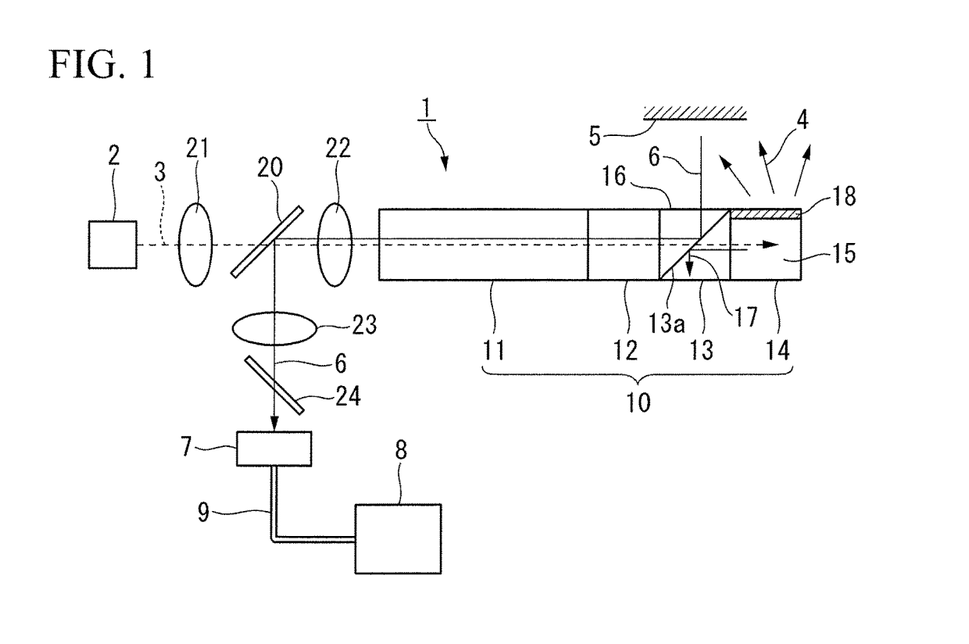
FIG. 1 is a configuration diagram showing an example of a side-viewing endoscope using a lighting structure related to a first embodiment of the invention.

FIG. 1 shows a side-viewing endoscope 1 using a lighting structure 10 related to a first embodiment of the invention.

The lighting structure 10 includes: an optical transmission medium 11 transmits pumping light 3 and image light 6 therethrough; an objective optical system 12 that is placed at the distal-end portion of the optical transmission medium 11; a wavelength conversion unit 14 including a fluorescent body 15 that receives the pumping light 3 transmitted through the optical transmission medium 11 and irradiates an object 5 with illuminating light 4; and a wavelength-selective reflective unit 13 including a wavelength filter 13a that selectively reflects a wavelength of the image light 6 and allows a wavelength of the pumping light 3 to selectively transmit therethrough.

The pumping light 3 is incident to the optical transmission medium 11 from a pumping light source 2, that is provided at the eyepiece side of the optical transmission medium 11 (left side in FIG. 1), and thereby transmitted to the object side (right side in FIG. 1).

The wavelength conversion unit 14 is provided on an extension line in the longitudinal direction of the optical transmission medium 11, and the pumping light 3 that is transmitted through the wavelength filter 13a is incident to the fluorescent body 15.

The fluorescent body 15 receives the pumping light 3 and radiates the illuminating light 4.

As a result of irradiating the object 5 that is lateral to the optical transmission medium 11 with the illuminating light 4, the object 5 is brightly lit, light that is reflected or scattered by the object 5 radiates as image light 6.

The wavelength filter 13a is provided to be incline with respect to the longitudinal direction of the optical transmission medium 11; when the image light 6 emitted from the object 5 is incident to the wavelength filter 13a through an objective part 16, the wavelength filter selectively reflects the image light 6 to be directed to the objective optical system 12.

The image light 6 is imaged by the objective optical system 12, incident to the optical transmission medium 11, and transmitted to the eyepiece side.

The wavelength filter 13a may be constituted of, for example, a thin film or the like such as a dielectric laminated film.

The wavelength filter 13a is arranged obliquely with respect to the longitudinal direction of the optical transmission medium 11 (optical axis) by being formed on an inclined face of a prism or being supported by a suitable member.

The inclination angle of the wavelength filter 13a with respect to the longitudinal direction of the optical transmission medium 11 is 45° in the drawing shown as an example but may be suitably set in accordance with the direction of the object 5.

For example, an angle of 30 to 60° may be adopted.

As a result of transmitting the pumping light 3 and the image light 6 through the same optical transmission medium 11, a diameter of the lighting structure 10 is easily reduced, as compared with in the case of separating an image transmission fiber from a lighting fiber.

For example, for the purpose of observing an inner blood vessel, the outer diameter of the distal-end portion can be reduced to be a diameter of 1 mm or less.

Furthermore, since the illuminating light 4 emitted from the fluorescent body 15 scatters in the fluorescent body 15, halation is difficult to occur, uniform illumination can be realized, and it is possible to make the illumination area large.

As the optical transmission medium 11, a multi-core fiber such as an image fiber or the like or a medium having flexibility such as a fiber bundle or the like is preferably used; the optical transmission medium may transmit light via a spatial beam or may use an optical system such as a relay lens or the like.

As a method of fixing the optical transmission medium 11, the objective optical system 12, the wavelength-selective reflective unit 13, and the wavelength conversion unit 14, a method of adhesively attaching edge surfaces to each other using a transparent adhesive with respect to a use wavelength, a method of performing fusion bonding without adhesive, a method of carrying out adhesion or fixation at a side face, or the like may be adopted depending on the type of structure, material, or the like of the members thereof.

In the lighting structure 10 of the embodiment, the wavelength-selective reflective unit 13 including a wavelength filter 13a that selectively reflects a wavelength of the image light 6 and allows a wavelength of the pumping light 3 to selectively transmit therethrough is provided between the fluorescent body 15 and the optical transmission medium 11.

Consequently, even in the case where the illuminating light 4 that is emitted from the fluorescent body 15 is emitted toward the optical transmission medium side 11 as returned light 17, the returned light 17 is reflected to be directed to the side that is different from the optical transmission medium 11 and the object 5, and it is possible to prevent contrast from being degraded.

As the pumping light source 2, a lamp, a laser, an LED, or the like may be adopted.

A wavelength of the pumping light 3 may be a wavelength in out of a visible region such as ultraviolet light (UV) and may be a visible light such as blue or purple.

In the case where the pumping light 3 is UV, a wavelength filter that allows UV to transmit therethrough and allows visible light to reflect can be preferably used as the wavelength filter 13a.

In the case where the pumping light 3 is visible light such as blue or purple, a wavelength of the pumping light 3 is preferably in a narrowband, and a filter that allows a wavelength of the pumping light to transmit therethrough and allows the wavelength of the other visible region to reflect therefrom is preferably used as the wavelength filter 13a.

In the case of a band-pass filter, a filter that has a pass band allowing a wavelength of the pumping light such as blue or purple to pass and reflects the wavelengths of both sides of the pass band is used.

In the case of a short-wavelength pass filter (high-pass filter), the visible light having a wavelength region close to that of UV is used as the pumping light, and a filter that has a pass band allowing a wavelength region including a wavelength of the pumping light and the wavelength shorter (higher in frequency) than thereof to pass and reflects the light having the wavelength longer than that of the pumping light.

Even in the case where the pumping light 3 is visible light, there is no problem in the quality of the image by use of a narrow-band pass filter.

The fluorescent body 15 that is provided at the wavelength conversion unit 14 and emits colored light or infrared light may be used depending on the purpose therefor, and a fluorescent body emitting white light is preferable for the intended use of observation with visible light.

As a fluorescent body emitting white light, for example, a fluorescent body used for a white LED, a white fluorescent lamp, or the like is used.

As a result of mixing three color of R, G, and B by one of or blending two or more of a red emission fluorescent body (R), a green emission fluorescent body (G), and a blue emission fluorescent body (B), it is also possible to obtain white light.

As a red fluorescent body that is excited by ultraviolet light, $YO_2S_2$: Eu, $Y_2O_3$: Eu, $YVO_4$: Eu, $Gd_2O_3$: Eu, (Y, Gd)$BO_3$: Eu, $YBO_3$: Eu, or the like may be adopted.

As a green fluorescent body that is excited by ultraviolet light, ZnS: Cu, Ag, $Zn_2SiO_4$: Mn, $BaAl_{12}O_{19}$: Mn, $BaMgAl_{16}O_{26}$: Eu, Mn, or the like may be adopted.

As a blue fluorescent body that is excited by ultraviolet light, $BaMgAl_{10}O_{17}$: Eu, $CaWO_4$: Pb, $Y_2SiO_5$: Ce, or the like may be adopted.

In the case where an excitation wavelength is blue, bluish-purple, purple, or the like, for example, a fluorescent body that is excited by blue light and thereby emits light such as yellow, red, or green is used, and it is possible to obtain white by mixing blue and yellow or by mixing blue, red, and green.

As a fluorescent body that can be excited by blue, YAG-based fluorescent body, a β-SiAlON phosphor, an α-SiAlON phosphor, $CaAlSiN_3$: Eu, or the like may be adopted.

In the case where a fluorescent substance including a material such as heavy metal ion, which may be harmful to a human body, by dispersing the fluorescent substance into a medium such as glass or resin, it is preferable to prevent a harmful material from being eluted.

It is preferable for glass, resin, or the like to have a high level of transparency in wavelength regions of the pumping light 3 or the illuminating light 4.

A mixture proportion is not particularly limited and the ratio indicated by "fluorescent material:glass, resin, or the like" is, for example, in the range of approximately 0.1:1 to 10:1.

In order to prevent the pumping light 3 from radiating to the object 5 along with the illuminating light 4 in the wavelength conversion unit 14, a pumping-light-removal filter 18 that reduces the intensity of the pumping light 3 by reflection or adsorption is preferably provided so as to cover at least the object side 5 of the wavelength conversion unit 14.

Particularly, in the case where the pumping light 3 is UV and the object 5 is a living tissue such as a human body, it is preferable that a UV cut filter be provided as the pumping-light-removal filter 18 or a coating containing a UV absorption agent be formed.

Additionally, in the case where, as a ultraviolet light reflection layer, white powder such as MgO, $SiO_2$, or $Al_2O_3$ is applied to and formed at a surface different from the object side 5, it is possible to improve excitation efficiency (refer to FIG. 3A to FIG. 3F, details thereof will be described below).

Since such inorganic oxide has a high UV transmissivity, a ultraviolet light reflection layer having a high degree of reflection due to dispersion, refraction, or the like (having a low percentage that converts UV into heat by absorption thereof) is obtained by forming a layer by use of powder.

In FIG. 1, each of the fluorescent body 15 that is provided at the wavelength conversion unit 14 and the pumping light source 2 that is provided at the eyepiece side is one, but a plurality pairs thereof may be provided.

For example, a first pumping light source that emits first pumping light and a second pumping light source that emits second pumping light are provided at the eyepiece side, and a first fluorescent body that receives the first pumping light and radiates illuminating light and a second fluorescent body that receives the second pumping light and radiates illuminating light are provided at the wavelength conversion unit.

As an example, it is preferable that the first pumping light source include a laser device emitting pumping light (bluish-purple, blue, and blue-green) having the wavelength range of 430 to 500 nm or the second pumping light source include a laser device emitting pumping light (purple and bluish-purple) having the wavelength range of 360 to 420 nm.

At this time, by causing one of the first pumping light source and the second pumping light source to be illuminated or by adjusting the intensity ratio indicated by "first pumping light:second pumping light" to be in the range of 100:0 to 0:100, it is possible to emit light from the wavelength conversion unit 14 to the object 5 in a state where first illuminating light and second illuminating light are mixed by a desired ratio (100:0 to 0:100).

Two fluorescent bodies are provided for each excitation wavelength and emit white light.

The fluorescent bodies emit white light slightly differently to each other, therefore, in order to obtain suitable white, by placing the fluorescent bodies in a predetermined order back and forth in the optical axial direction or by adjusting the thickness of each fluorescent body, it is possible to realize a white light source with a high level of color rendering property.

Where the aforementioned first pumping light source and the first fluorescent body are a first unit and the aforementioned second pumping light source and the second fluorescent body are a second unit, it is preferable that a fluorescent material (fluorescent body used for the first pumping light source) in the first unit be formed by combining rare earth aluminate and oxynitride or nitride.

Additionally, it is preferable that a fluorescent material (fluorescent body used for the second pumping light source) in the second unit be formed by combining rare earth aluminate and alkaline earth metal halogen apatite or by combining rare earth aluminate, alkaline earth metal halogen apatite and oxynitride or nitride.

As rare earth aluminate, LAG (lutetium aluminum garnet), YAG (yttrium aluminum garnet), or the like may be adopted.

As oxynitride or nitride, SESN (strontium silicon nitride), SCESN (calcium strontium silicon nitride), CESN (calcium silicon nitride), or the like may be adopted.

As alkaline earth halogen apatite, CCA (calcium chlorapatite), SCA (barium chlorapatite), or the like may be adopted.

The eyepiece-side optical system includes a wavelength filter 20 provided between the pumping light source 2 and the optical transmission medium 11, allows the pumping light 3 emitted from the pumping light source 2 to transmit therethrough and to be thereby incident to the optical transmission medium 11, reflects the image light 6 that is transmitted through the optical transmission medium 11, and transmit this to a camera 7 such as a CCD.

A noise removal filter 24 that removes noise from the image light 6 can be provided between the wavelength filter 20 and the camera 7.

As the noise removal filter 24, a filter that removes near-infrared light (NIR) and ultraviolet light (UV/NIR cut filter) or a three-wavelength filter that allows a wavelength region compliant with the sensitivity of the camera 7 to transmit therethrough and makes transmissivity of wavelength regions of noise low may be adopted.

The camera 7 transmits an electrical signal, into which the image light is converted, to a monitor 8 via wiring 9, and an image thereof can be observed on the monitor 8.

In FIG. 1, reference numerals 21 to 23 are lenses.

The pumping light 3 emitted from the pumping light source 2 is imaged by the lenses 21 and 22 and can be incident to the optical transmission medium 11.

Furthermore, the image light 6 emitted from the optical transmission medium 11 is imaged by the lenses 22 and 23 and can be incident to the camera 7.

As the monitor 8, a liquid crystal display device, a CRT, or the like may be used.

The eyepiece-side optical system is not limited to a relay optical system such that the pumping light or the image light is transmitted by one-on-one relaying as shown in drawings; an imaging optical system that forms an image on the camera 7 from the image light 6 emitted from an edge surface of the optical transmission medium 11 or an incident optical system that allows the pumping light 3 to be incident to the edge surface of the optical transmission medium 11 from the pumping light source 2 may be used.

Figure 2:
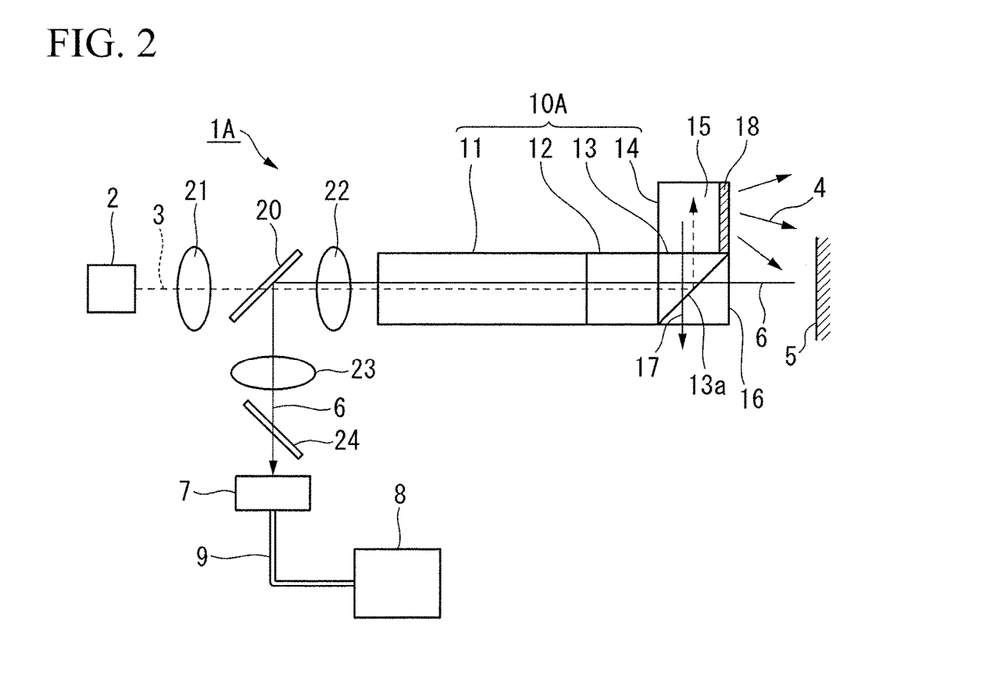
FIG. 2 is a configuration diagram showing an example of a direct-view endoscope using a lighting structure related to a second embodiment of the invention.

FIG. 2 shows a direct-view endoscope 1A using a lighting structure 10A related to a second embodiment of the invention.

The lighting structure 10A includes: an optical transmission medium 11 transmits pumping light 3 and image light 6 therethrough; an objective optical system 12 that is placed at the distal-end portion of the optical transmission medium 11; a wavelength conversion unit 14 including a fluorescent body 15 that receives the pumping light 3 transmitted through the optical transmission medium 11 and irradiates an object 5 with illuminating light 4; and a wavelength-selective reflective unit 13 including a wavelength filter 13a that selectively reflects a wavelength of the pumping light 3 and allows a wavelength of the image light 6 to selectively transmit therethrough.

In terms of difference in the characteristics of the wavelength filter 13a in addition to in the terms of the objective part 16 that faces the object 5 and is provided on an extension line in the longitudinal direction of the optical transmission medium 11 and the wavelength conversion unit 14 that has the fluorescent body 15 and is provided lateral to the optical transmission medium 11, the lighting structure 10A of the embodiment is different from that in FIG. 1.

According to the endoscope 1A including the lighting structure 10A of the embodiment, even in the case where the illuminating light 4 emitted from the fluorescent body 15 is emitted to the optical transmission medium side 11 as the returned light 17, since the wavelength-selective reflective unit 13 including a wavelength filter 13a that selectively reflects a wavelength of the pumping light 3 and allows a wavelength of the image light 6 to selectively transmit therethrough is provided between the fluorescent body 15 and the optical transmission medium 11, the returned light 17 passes through the wavelength filter 13a in the direction different from that of both the optical transmission medium 11 and the object 5, and it is thereby possible to prevent contrast from being degraded.

It is preferable to provide a mirror or a filter, which adjusts a direction, an intensity, a transparency range, or the like of the pumping light 3 or the illuminating light 4, at the wavelength conversion unit 14.

For example, as shown in FIG. 1 or 2, the pumping-light-removal filter 18 that prevents the pumping light 3 from radiating to the object 5 may be provided on an outer surface of at least the object side 5 of the wavelength conversion unit 14.

In the case where the pumping light is ultraviolet light, a ultraviolet light reflection layer that is formed and coated with white powder such as $MgO$, $SiO_2$, or $Al_2O_3$ thereon may be formed as a mirror.

Figure 3A:
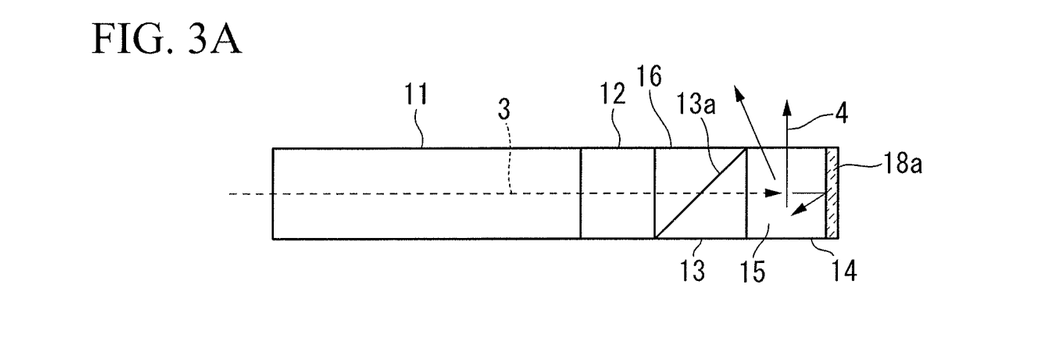
FIG. 3A is a configuration diagram showing an example of a lighting structure in which a mirror or a filter is provided on the front-end face of the optical transmission medium in an extension line in the longitudinal direction thereof in the wavelength conversion unit.

A mirror 18a or a filter shown in FIG. 3A is provided on a front-end face of the wavelength conversion unit 14 and on an extension line in the longitudinal direction of the optical transmission medium 11, causes the pumping light 3 or the illuminating light 4 to be reflected, and thereby increases the efficiency of conversion from the pumping light 3 into the illuminating light 4 or can increase the intensity of the illuminating light 4 proceeding to the object.

Figure 3B:
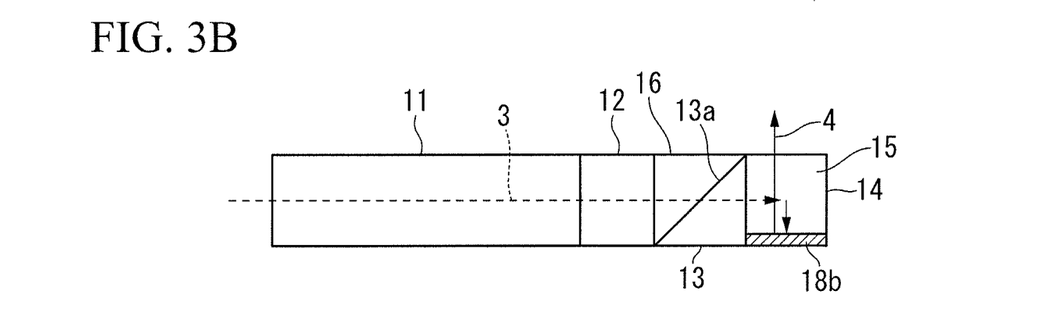
FIG. 3B is a configuration diagram showing an example of a lighting structure in which a mirror or a filter is provided on the side surface on the opposite side of the object in the wavelength conversion unit.

A mirror 18b or a filter shown in FIG. 3B is provided on the side surface of the wavelength conversion unit 14 on the opposite side of the object, causes the pumping light 3 or the illuminating light 4 to be reflected, and thereby increases the efficiency of conversion from the pumping light 3 into the illuminating light 4 or can increase the intensity of the illuminating light 4 proceeding to the object.

Figure 3C:
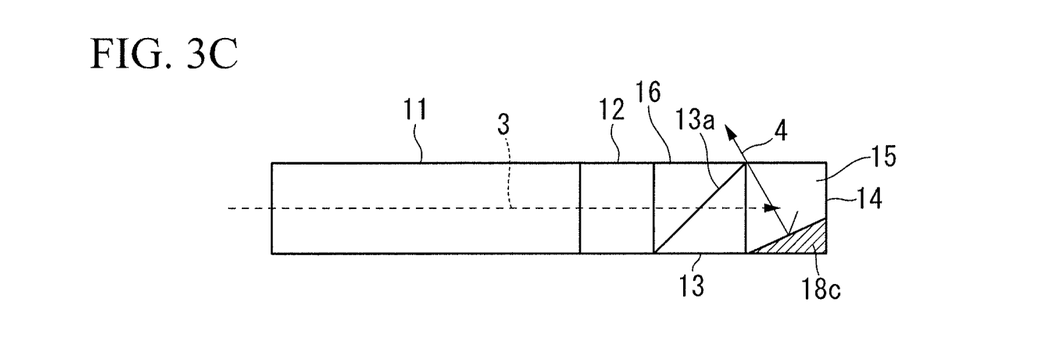
FIG. 3C is a configuration diagram showing an example of a lighting structure in which a mirror or a filter is provided so as to be inclined with respect to the side surface on the opposite side of the object in the wavelength conversion unit.

A mirror 18c or a filter shown in FIG. 3C is provided so as to be inclined with respect to the side surface the wavelength conversion unit 14 on the opposite side of the object and is configured to cause more reflected light to be directed to the object.

Figure 3D:
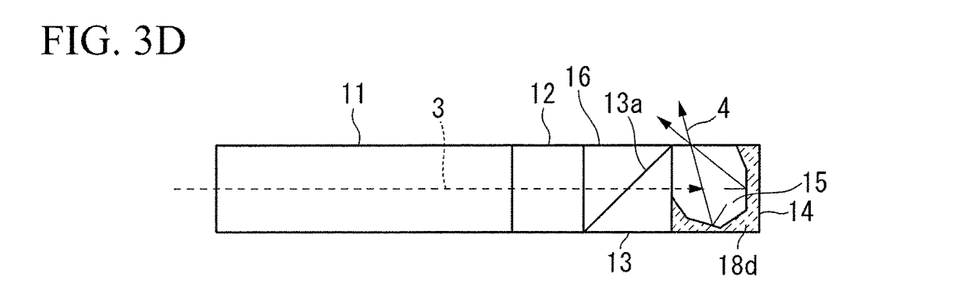
FIG. 3D is a configuration diagram showing an example of a lighting structure in which a mirror or a filter is provided so as to surround the front-end face of the optical transmission medium in an extension line in the longitudinal direction thereof, and the side surface on the opposite side of the object, and the like in the wavelength conversion unit.

A mirror 18d or a filter shown in FIG. 3D is provided so as to open a portion that is necessary for entering of the pumping light 3 and emission of the illuminating light 4 to the object and so as to surround the front-end face that is on an extension line in the longitudinal direction of the optical transmission medium 11, the side surface on the opposite side of the object, or the like.

Consequently, it is possible to effectively increase the efficiency of conversion from the pumping light 3 into the illuminating light 4 or the intensity of the illuminating light 4 proceeding to the object.

Figure 3E:
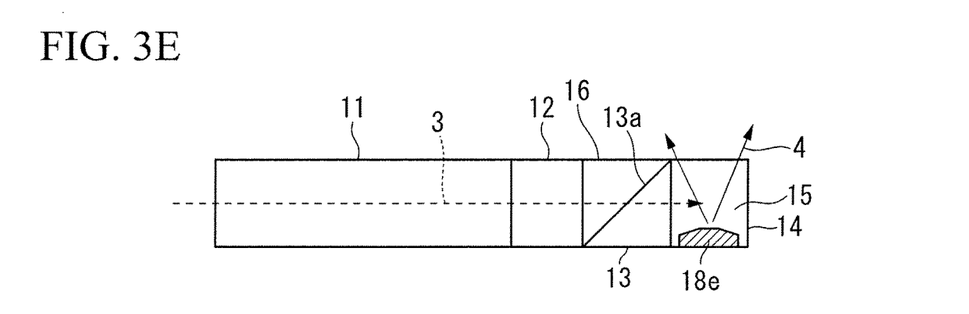
FIG. 3E is a configuration diagram showing an example of a lighting structure in which a mirror or a filter is provided so as to include a reflection surface that protrudes toward the inside of the wavelength conversion unit.

A mirror 18e or a filter shown in FIG. 3E has a projecting reflection surface that is directed to the inside of the wavelength conversion unit 14 and can diffuse reflected light.

Figure 3F:
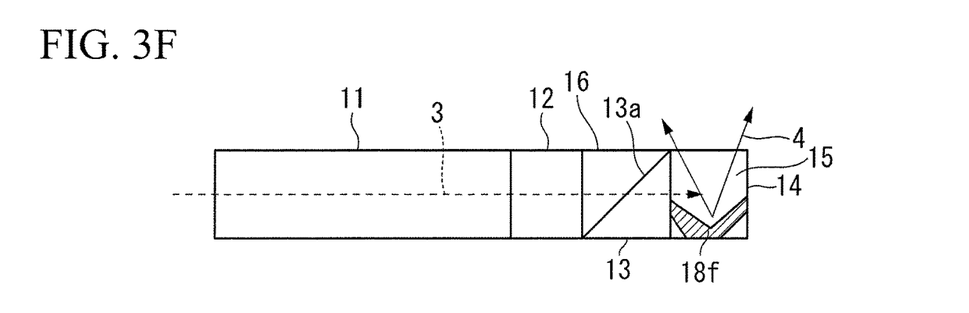
FIG. 3F is a configuration diagram showing an example of a lighting structure in which a mirror or a filter is provided so as to include a plurality of reflection surfaces that face the inside of the wavelength conversion unit.

A mirror 18f or a filter shown in FIG. 3F has a plurality of reflection surfaces that are directed to the inside of the wavelength conversion unit 14 and can diffuse reflected light.

Such filters or mirrors may be attached to the periphery of the fluorescent body 15 or may be provided with a necessary function as a result of processing the surface of the fluorescent body 15 or the surface of the material in which the fluorescent body 15 is dispersed.

In order to prevent the returned light 17 from being incident to the optical transmission medium 11, an aperture, an iris, or a filter that serves as a means of reducing an amount of the returned light 17 may be provided between the wavelength-selective reflective unit 13 and the wavelength conversion unit 14.

Figure 4A:
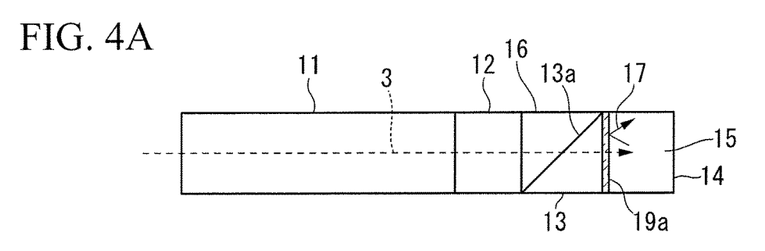
FIG. 4A is a configuration diagram showing an example of providing a wavelength filter that allows a wavelength region of pumping light to transmit therethrough and reflects or absorbs a wavelength region of illuminating light, on an entire surface between a wavelength-selective reflective unit and a wavelength conversion unit.

A filter 19a shown in FIG. 4A is a wavelength filter that allows a wavelength of the pumping light 3 to transmit therethrough, reflects or absorbs a wavelength of the illuminating light 4, and can be provided over the whole surface between the wavelength-selective reflective unit 13 and the wavelength conversion unit 14.

Figure 4B:
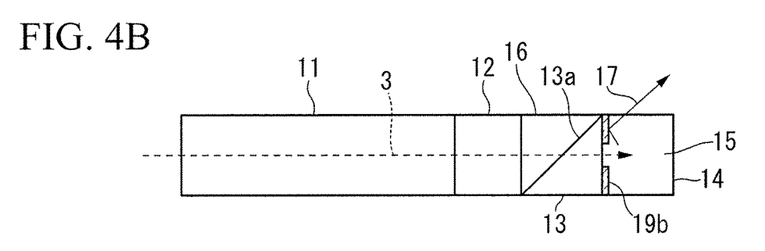
FIG. 4B is a configuration diagram showing an example of providing an aperture, an iris, or a filter, in which the central portion thereof on the cross section perpendicular to the longitudinal direction of the optical transmission medium is opened so as to allows pumping light to transmit therethrough, between the wavelength-selective reflective unit and the wavelength conversion unit.

As shown in FIG. 4B, between the wavelength-selective reflective unit 13 and the wavelength conversion unit 14, the aperture, the iris, or the filter 19b has a central portion of the cross section thereof perpendicular to the longitudinal direction of the optical transmission medium 11 where the central portion opens so as to allow the pumping light 3 to pass therethrough.

Figure 4C:
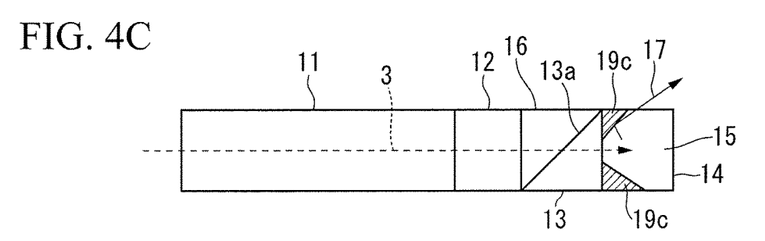
FIG. 4C is a configuration diagram showing an example of providing an aperture, an iris, or a filter, which includes: an opening portion that is provided at the central portion thereof on the cross section perpendicular to the longitudinal direction of the optical transmission medium and allows pumping light to transmit therethrough; and an inclined reflection surface that is provided at a peripheral portion thereof, between the wavelength-selective reflective unit and the wavelength conversion unit.

As shown in FIG. 4C, between the wavelength-selective reflective unit 13 and the wavelength conversion unit 14, the aperture, the iris, or the filter 19b has an opening portion that is provided at a central portion of the cross section thereof perpendicular to the longitudinal direction of the optical transmission medium 11 where the opening portion allows the pumping light 3 to pass therethrough and where an inclined reflection surface is provided at the peripheral portion thereof.

Figure 4D:
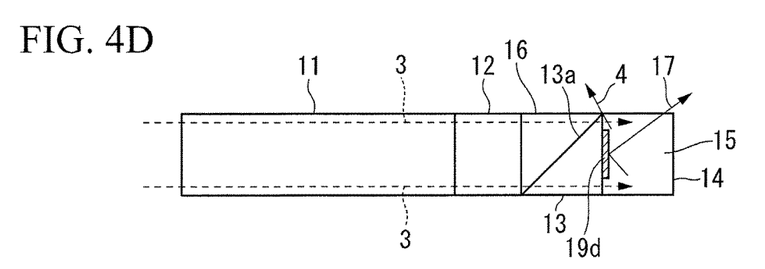
FIG. 4D is a configuration diagram showing an example of providing an aperture, an iris, or a filter, in which the peripheral portion thereof on the cross section perpendicular to the longitudinal direction of the optical transmission medium is opened, between the wavelength-selective reflective unit and the wavelength conversion unit.

As shown in FIG. 4D, between the wavelength-selective reflective unit 13 and the wavelength conversion unit 14, the aperture, the iris, or the filter 19d has an opened peripheral portion of the cross section thereof perpendicular to the longitudinal direction of the optical transmission medium 11.

The means of reducing an amount of the returned light 17 allows the pumping light 3 to pass therethrough within a fixed opening range, may be an aperture (limiting aperture) or an iris (iris diaphragm) that prevents the pumping light 3 or the illuminating light 4 from passing therethrough at the periphery of the opening, or may be a wavelength filter that allows a wavelength of the pumping light 3 to transmit therethrough and reflects or absorbs a wavelength of the illuminating light 4.

In the case where the aperture, the iris, or the filters 19b, 19c, and 19d reflect the pumping light 3, the pumping light 3 is incident to the wavelength conversion unit 14 through the limited opening portion; however, it is possible to increase the efficiency of the pumping light 3 that is incident to the fluorescent body 15.

When the pumping light 3 is incident to the optical transmission medium 11 from the eyepiece system, the pumping light 3 is made incident to part of the cross-sectional area of the optical transmission medium 11, and the light can be thereby guided.

Figure 5:
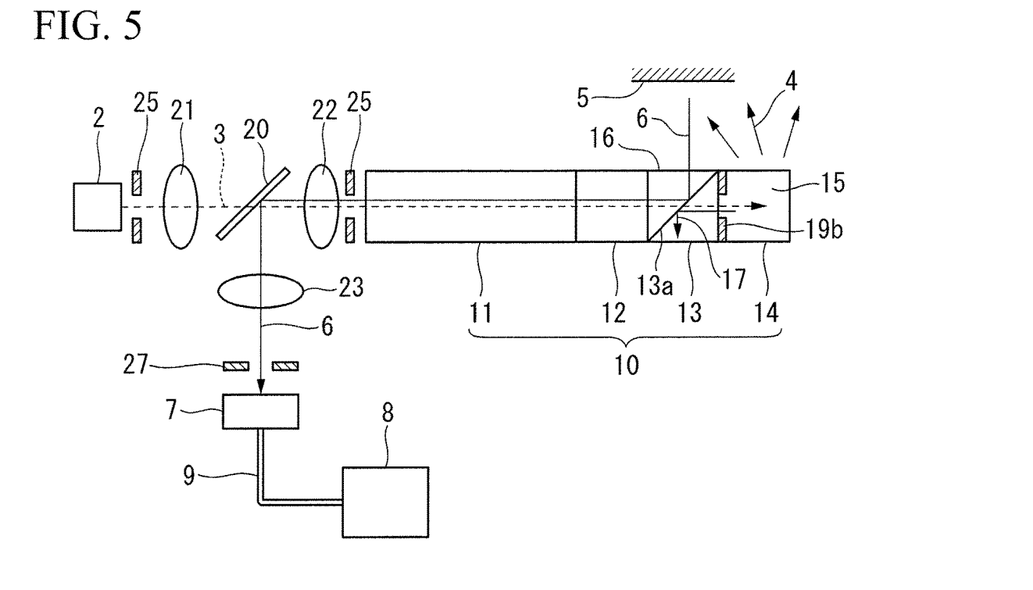
FIG. 5 is a configuration diagram showing an example of only guiding pumping light to the central portion of the cross section of the optical transmission medium.

FIG. 5 shows an example of guiding the pumping light 3 to only the central portion of the cross section of the optical transmission medium 11.

Such configuration can be realized by, for example, providing one, two, or more filters or masks 25 between the pumping light source 2 and the optical transmission medium 11; the filters or masks allow the pumping light 3 to transmit therethrough so as to correspond to the central portion of the cross section of the optical transmission medium 11, prevent the pumping light 3 from being incident to the peripheral portion of the cross section of the optical transmission medium 11, and have an orbicular zone.

In this case, between the wavelength-selective reflective unit 13 and the wavelength conversion unit 14, as a result of combining the iris or the filter 19b which has the central portion of the cross section thereof perpendicular to the longitudinal direction of the optical transmission medium 11 where the central portion opens so as to allow the pumping light 3 to pass therethrough, it is possible to prevent unnecessary diffusion of the pumping light 3, and therefore preferable.

As described above, by the wavelength-selective reflective unit 13, the illuminating light 4 included in the returned light 17 is prevented from being incident to the optical transmission medium 11; however, in the case where the returned light 17 includes part of the pumping light 3, there is a concern that the light passes through the wavelength-selective reflective unit 13 and is transmitted from the object side to the eyepiece side through the optical transmission medium 11.

In preparation for this case, a filter or a mask 27 that allows the image light 6 to transmit therethrough, prevents the pumping light 3, and has an orbicular zone is provided in front of the camera 7 and at the central portion of the cross section perpendicular to the optical axis, and it is possible to suppress the influence of the pumping light 3 to the camera 7.

In the case where a wavelength of the pumping light 3 does not adversely affect the camera 7, the filter or the mask 27 that is in front of the camera 7 is not necessary.

Figure 6:
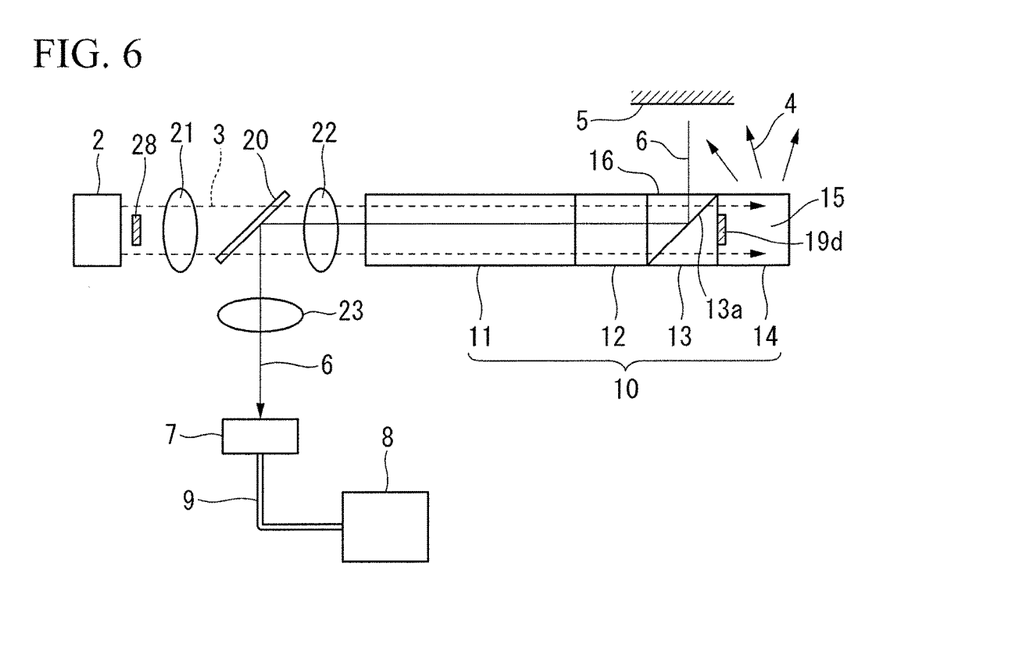
FIG. 6 is a configuration diagram showing an example of only guiding pumping light to the peripheral portion of the cross section of the optical transmission medium.

FIG. 6 shows an example of only guiding the pumping light 3 to the peripheral portion of the cross section of the optical transmission medium 11.

Such configuration can be realized by, for example, providing one, two, or more filters or masks 28 between the pumping light source 2 and the optical transmission medium 11; the filters or masks allow the pumping light 3 to transmit therethrough so as to correspond to the peripheral portion of the cross section of the optical transmission medium 11, prevent the pumping light 3 from being incident to the central portion of the cross section of the optical transmission medium 11, and have an orbicular zone.

In this case, between the wavelength-selective reflective unit 13 and the wavelength conversion unit 14, as a result of combining the iris or the filter 19d which have the peripheral portion of the cross section thereof perpendicular to the longitudinal direction of the optical transmission medium 11 where the peripheral portion opens so as to allow the pumping light 3 to pass therethrough, it is possible to prevent unnecessary diffusion of the pumping light 3, and therefore preferable.

Particularly, in the case where a wavelength of the pumping light 3 is blue or purple and overlaps part of a wavelength region of the image light 6, when the pumping light 3 is light-guided to only the peripheral portion of the cross section of the optical transmission medium 11, the pumping light 3 is not light-guided to the central portion of the cross section of the optical transmission medium 11, therefore, it is possible to suppress the influence to an image which is due to reflection of the pumping light 3 (blue or purple) at the edge surface or the like of the optical transmission medium 11.

Figure 7:
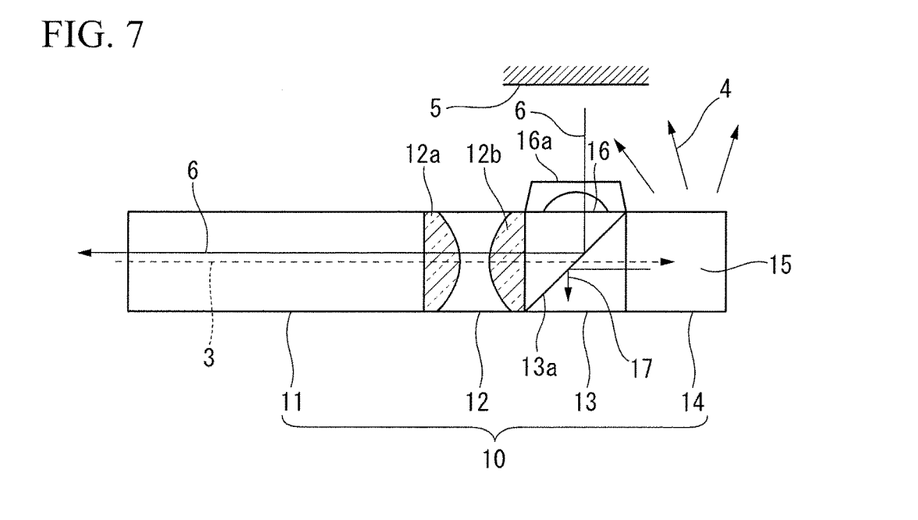
FIG. 7 is a configuration diagram showing an example of providing an optical system between a wavelength-selective reflective unit and an object.

FIG. 7 shows an example of providing an object lens 16a, that serves as an optical system, at the objective part 16 that is between the wavelength-selective reflective unit 13 and the object 5.

In the objective optical system 12, it is possible to use combined lenses 12a and 12b for image formation.

As a lens used for the objective optical system 12, a cylindrical gradient index lens (SELFOC (registered trademark) of Nippon Sheet Glass Co., Ltd., rod lens (registered trademark) of Mitsubishi Rayon Co., Ltd., or the like; a radial graded index lens that has a refractive index profile in the radial direction thereof and is determined by JIS C 5934 (General rules of lenses for fiber optic transmission), referred to as GRIN lens) may also be used.

Since the foregoing cylindrical lens has edge surfaces to which light is incident, or from which light is emitted, and which are provided at both cylindrical bottom faces, it is also possible to preferably use the cylindrical lens as the optical transmission medium 11 by using one cylindrical lens or by arranging two or more cylindrical lenses in a row.

If the objective optical system 12 is formed in a cylindrical shape that is on the same axis as that of the optical transmission medium 11 and has the same diameter as that of the optical transmission medium, since a difference in level is not formed on the side face of the lighting structure 10, it is advantageous to reduce a diameter of an observation device such as endoscope.

Figure 8:
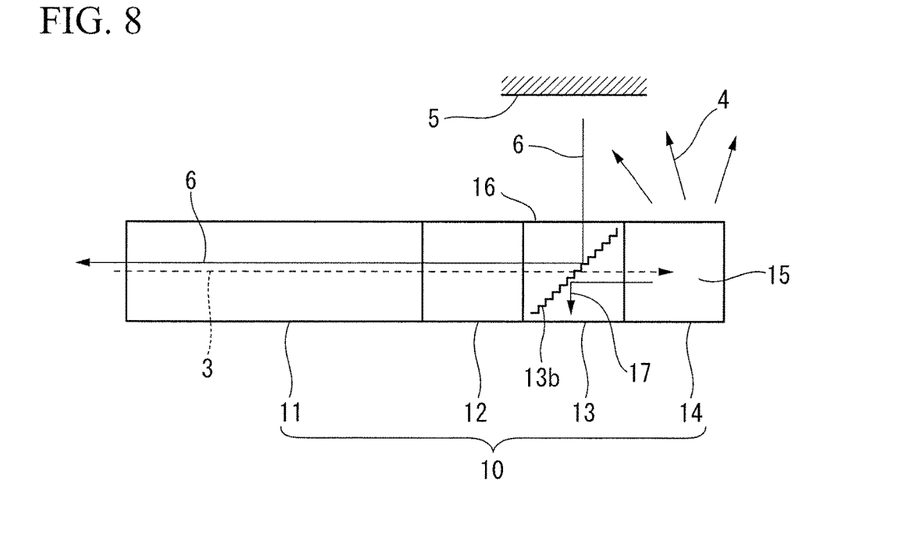
FIG. 8 is a configuration diagram showing an example using a grating at a wavelength-selective reflective unit.

FIG. 8 shows an example of using a grating 13b as the wavelength-selective reflective unit 13.

Figure 9:
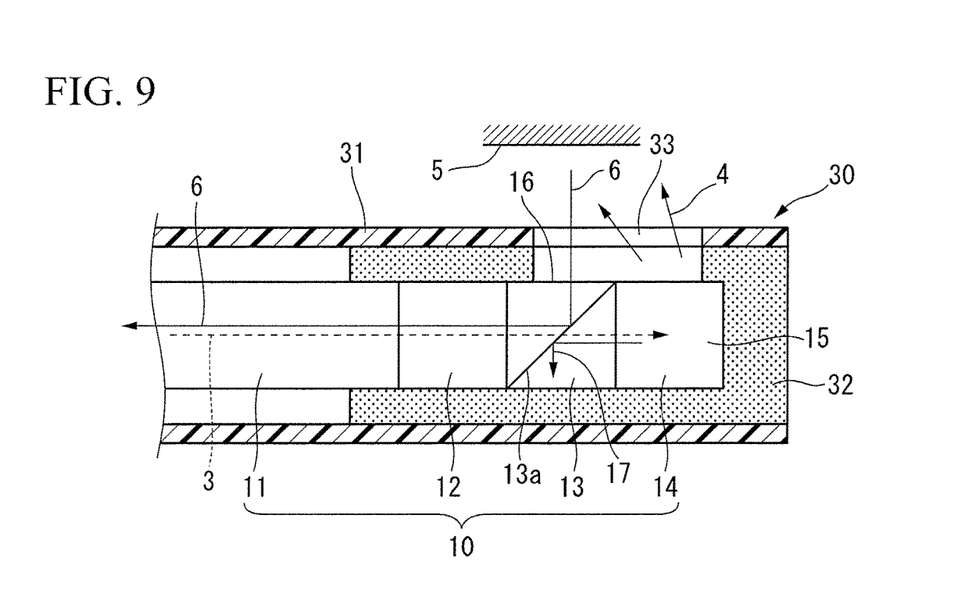
FIG. 9 is a cross-sectional view showing an example of a distal-end portion of an endoscope using the lighting structure of the invention.
Figure 10:
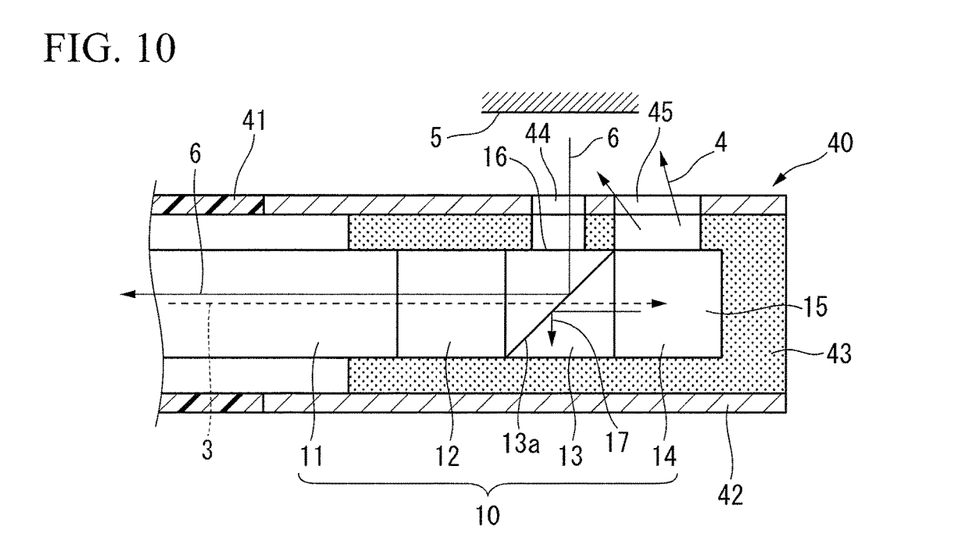
FIG. 10 is a cross-sectional view showing an example of a distal-end portion of an endoscope using the lighting structure of the invention.

FIGS. 9 and 10 show an example of a distal-end portion of an endoscope using the above-described lighting structure 10.

In an endoscope 30 shown in FIG. 9, the periphery of the lighting structure 10 is covered with an elastic tube 31 and the internal side of the tube 31 is sealed by a resin 32.

A window 33 that allows the illuminating light 4 emitted from the wavelength conversion unit 14 to the object 5 to pass therethrough and allows the image light 6 incident to the objective part 16 from the object 5 to pass therethrough is formed on the side face of the tube 31.

In an endoscope 40 shown in FIG. 10, the periphery of the lighting structure 10 is covered with an elastic tube 41 and a rigid sleeve 42, and the inner side of the sleeve 42 is sealed by a resin 43.

The sleeve 42 is provided so as to surround at least the objective optical system 12, the wavelength-selective reflective unit 13, and the periphery of the wavelength conversion unit 14, and the most portion of the periphery of the optical transmission medium 11 is surrounded by the elastic tube 41.

A window 45 that allows the illuminating light 4 emitted from the wavelength conversion unit 14 to the object 5 to pass therethrough and a window 44 that allows the image light 6 incident to the objective part 16 from the object 5 to pass therethrough are formed on the side face of the sleeve 42.

It is preferable that the parts of the windows 33, 44, and 45 be tightly sealed by transparent resin, glass, a lens, or the like.

In the resins 32 and 43, glass, or the like that protect the lighting structure 10, a portion that allows the illuminating light 4 or the image light 6 to transmit therethrough is necessary to be transparent, and the other portions may be devitrified.

A portion that is not necessary to transmit the illuminating light 4 or the image light 6 may be made of a light shielding material such as black.

The tubes 31 and 41 can be formed of rubber, elastic resin, or the like.

The sleeve 42 can be formed of metal, glass, resin, or the like.

For example, for the purpose of observing an inner blood vessel, the outer diameter of the distal-end portion of the endoscope such as the tube 31 or the sleeve 42 can be reduced to be a diameter of 1 mm or less.

As described above, the invention is described with reference to preferred embodiments; however, the invention is not limited to the above embodiments, and various modifications may be made without departing from the scope of the invention.

In the case where a wavelength of the image light 6 is in a visible region, UV light or a common wavelength-band such as blue or purple is preferably used as a wavelength of the pumping light 3; however, in the case where a wavelength of the image light 6 is in an infrared region, visible light may be used as a wavelength of the pumping light 3.

In this case, the wavelength conversion unit 14 receives the pumping light 3 of a visible region and irradiates the object 5 with illuminating light 4 (irradiation light) of an infrared region.

It is preferable that the camera 7 can image-capture an infrared image; however, as a result of providing a wavelength conversion element that converts infrared light into visible light, it is also possible to take an image after conversion of an infrared image to a visible image.

The wavelength conversion element may convert input light into light having a shorter wavelength and output the light or may convert input light into light having a longer wavelength and output the light, and for example, may serves as a wavelength conversion element such as a harmonic generation element which is disposed at the wavelength conversion unit.

The input light which is to be input to a wavelength conversion element is not limited to pumping light that excites a wavelength conversion element and may be applicable to wavelength conversion by use of methods other than excitation.

It is preferable that the output light that is output from a wavelength conversion element be appropriately used for illumination to or irradiation of an observed object; and the output light may be in narrowband or in broadband.

In the case where illuminating light is visible light, broadband white light is preferable.

What is claimed is:

1. A lighting structure comprising:
   an image fiber that transmits pumping light and image light therethrough;
   an objective optical system that is disposed at a distal-end portion of the image fiber;
   a wavelength conversion unit comprising a fluorescent body that receives the pumping light transmitted through the image fiber and irradiates an object with illuminating light, the wavelength conversion unit being provided on an extension line in a longitudinal direction of the image fiber;
   a wavelength-selective reflective unit that selectively reflects one of a wavelength of the pumping light and a wavelength of the image light, thereby emits pumping light that is incident thereto through the image fiber into the fluorescent body and emits image light that is incident from the object into the image fiber through the objective optical system;
   a first wavelength filter which allows the pumping light to transmit therethrough and to be thereby incident to the image fiber, the first wavelength filter configured to reflect the image light that is transmitted through the image fiber to an image-sensing device; and
   a noise removal filter provided between the first wavelength filter and the image-sensing device, the noise removal filter removing noise from the image light.

2. The lighting structure according to claim 1, wherein the pumping light is ultraviolet light, and
   the wavelength-selective reflective unit comprises a second wavelength filter that allows the ultraviolet light to transmit therethrough and allows visible light to reflect.

3. The lighting structure according to claim 1, wherein the pumping light is blue or purple visible light, and
   the wavelength-selective reflective unit comprises a bandpass filter that allows a wavelength of the pumping light to transmit therethrough.

4. The lighting structure according to claim 1, wherein the objective optical system is formed in a cylindrical shape that is on the same axis as that of the image fiber and has the same diameter as that of the image fiber.

5. The lighting structure according to claim 1, wherein the noise removal filter is provided at an eyepiece system.

6. The lighting structure according to claim 1, wherein the fluorescent body is dispersed in glass or resin.

7. The lighting structure according to claim 1, wherein the wavelength conversion unit comprises a mirror or a filter which adjusts a direction, an intensity, or a transparency range of the pumping light or the illuminating light.

8. The lighting structure according to claim 1, further comprising an aperture, an iris, or a filter that prevents returned light from being incident to a front end of the image fiber, serves as a means of reducing an amount of the returned light, and is provided between the wavelength-selective reflective unit and the wavelength conversion unit.

9. The lighting structure according to claim 1, wherein the pumping light is incident to a part of a cross-sectional area of the optical transmission medium and light guiding is thereby carried out.

10. The lighting structure according to claim 1, further comprising a mask or a filter which prevents noise light, that is from the optical transmission medium, from being incident to an image-sensing device such as a camera that converts the image light into an electrical signal.

11. An endoscope comprising the lighting structure according to claim 1.

12. The endoscope according to claim 11 being a side-viewing endoscope.

13. The endoscope according to claim 11, wherein an outer diameter of the distal-end portion is a small diameter of 1 mm or less.

14. The endoscope according to claim 11 used for observing an inner blood vessel.

* * * * *